(12) United States Patent
Wu et al.

(10) Patent No.: US 9,962,674 B2
(45) Date of Patent: May 8, 2018

(54) HYBRID MICROCAPSULES

(71) Applicant: Firmenich SA, Geneva (CH)

(72) Inventors: Yongtao Wu, Shanghai (CN); Lahoussine Ouali, Geneva (CH)

(73) Assignee: Firmenich SA, Geneva (CH)

( * ) Notice: Subject to any disclaimer, the term of this patent is extended or adjusted under 35 U.S.C. 154(b) by 43 days.

(21) Appl. No.: 15/106,151

(22) PCT Filed: Dec. 17, 2014

(86) PCT No.: PCT/EP2014/078324
§ 371 (c)(1),
(2) Date: Jun. 17, 2016

(87) PCT Pub. No.: WO2015/091705
PCT Pub. Date: Jun. 25, 2015

(65) Prior Publication Data
US 2016/0354749 A1 Dec. 8, 2016

(30) Foreign Application Priority Data
Dec. 19, 2013 (EP) ..................... 13198298

(51) Int. Cl.
| *A61K 8/00* | (2006.01) |
| *A61L 9/04* | (2006.01) |
| *B01J 13/16* | (2006.01) |
| *B01J 13/02* | (2006.01) |
| *B01J 13/14* | (2006.01) |
| *C11D 3/50* | (2006.01) |
| *A61K 8/04* | (2006.01) |
| *A61K 8/19* | (2006.01) |
| *A61K 8/24* | (2006.01) |
| *A61K 8/25* | (2006.01) |
| *A61K 8/29* | (2006.01) |
| *A61K 8/40* | (2006.01) |
| *A61Q 19/10* | (2006.01) |
| *C11B 9/00* | (2006.01) |

(52) U.S. Cl.
CPC ............. *B01J 13/16* (2013.01); *A61K 8/042* (2013.01); *A61K 8/19* (2013.01); *A61K 8/24* (2013.01); *A61K 8/25* (2013.01); *A61K 8/29* (2013.01); *A61K 8/40* (2013.01); *A61Q 19/10* (2013.01); *B01J 13/02* (2013.01); *B01J 13/14* (2013.01); *C11B 9/0034* (2013.01); *C11B 9/0061* (2013.01); *C11B 9/0065* (2013.01); *C11D 3/505* (2013.01)

(58) Field of Classification Search
CPC .. B01J 13/16; B01J 13/02; A61K 8/25; A61K 8/19; A61K 8/40; A61K 8/042; A61K 8/29; A61K 8/24; C11B 9/0065; C11B 9/0034; C11B 9/0061; A61Q 19/10; C11D 3/505
USPC ........................................... 512/4, 1
See application file for complete search history.

(56) References Cited

U.S. PATENT DOCUMENTS

| 8,778,867 | B2 * | 7/2014 | Ouali | ............ | A61K 8/11 |
| | | | | | 512/2 |
| 2007/0202063 | A1 | 8/2007 | Dihora et al. | | |
| 2011/0200658 | A1 * | 8/2011 | Mulqueen | .............. | A01N 25/28 |
| | | | | | 424/408 |
| 2015/0190774 | A1 * | 7/2015 | Phipps | ............. | A01N 25/28 |
| | | | | | 427/213.34 |

FOREIGN PATENT DOCUMENTS

| EP | 1 741 775 A1 | 1/2007 | | |
| GB | 2 432 843 A | 6/2007 | | |
| GB | 2 432 850 A | 6/2007 | | |
| GB | 2 432 851 A | 6/2007 | | |
| GB | 2 432 852 A | 6/2007 | | |
| WO | 98/50011 A1 | 11/1998 | | |
| WO | 2005/054422 A1 | 6/2005 | | |
| WO | 2007/062733 A1 | 6/2007 | | |
| WO | 2007/062833 A1 | 6/2007 | | |
| WO | 2008/016684 A1 | 2/2008 | | |
| WO | 2009/063257 A2 | 5/2009 | | |
| WO | 2010/070602 A2 | 6/2010 | | |
| WO | 2011/154893 A1 | 12/2011 | | |
| WO | 2012/084904 A1 | 6/2012 | | |
| WO | 2013/174615 A2 | 11/2013 | | |
| WO | WO-2013182855 A2 * | 12/2013 | ............. | A01N 25/28 |

OTHER PUBLICATIONS

International Search Report and Written Opinion, Appl. No. PCT/EP2014/078324, dated Feb. 24, 2015.

* cited by examiner

*Primary Examiner* — Jessica Whiteley
(74) *Attorney, Agent, or Firm* — Winston & Strawn LLP

(57) ABSTRACT

The present invention relates to a process for the preparation of organic-inorganic microcapsules, with a flavor or fragrance core and a hybrid shell composed of at least two types of inorganic particles that are cross-linked. Microcapsules obtained by said process are also an object of the invention. Consumer products comprising said capsules, in particular perfumed consumer products in the form of home care or personal care products, are also part of the invention.

20 Claims, 3 Drawing Sheets

HYBRID MICROCAPSULES

This application is a 371 filing of International Patent Application PCT/EP2014/078324 filed 17 Dec. 2014, which claims the benefit of European patent application no. 13198298.5 filed 19 Dec. 2013.

TECHNICAL FIELD

The present invention relates to a process for the preparation of organic-inorganic microcapsules, also called "hybrid" microcapsules with a flavour or fragrance core and a hybrid shell composed of at least two types of inorganic particles that are cross-linked. Microcapsules obtained by said process are also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as poly(amines) and poly(isocyanates), has been described as a way to improve stability of microcapsules. WO2011/154893 discloses for instance a process for the preparation of polyurea microcapsules using a combination of aromatic and aliphatic polyisocyanates in specific relative concentrations.

Stabilization of oil/water interfaces with inorganic particles has been described in so-called Pickering emulsions. In this context, functionalization of inorganic particles to allow their cross-linking is known. For instance, Pickering emulsions cross-linked from an outer water phase with polyelectrolytes providing electrostatic interactions have been the object of prior disclosures (Li Jian et al. in Langmuir (2010), 26(19), 15554-15560). However, such systems are very likely to dissociate in a surfactant base or in ethanol over time as electrostatic interactions are insufficient to promote stability. Covalent cross-linking has also been described in relation with Pickering emulsion in the preparation of colloidosomes. In particular, the use of diisocyanates as cross-linker has been disclosed in scientific publications. WO2009/063257 also describes the use of polyisocyanates as possible cross-linker for surface-modified inorganic particles in order to prepare microcapsules with increased level of protection from u.v. light for the contents. These products are typically intended for agrochemical applications. This type of system is not suitable for perfume encapsulation. In fact, in order to maintain a good morphology and permeability of the microcapsules, an excess of surface-modified inorganic particles is needed. Another problem is that these microcapsules show little margin for size adjustment. Furthermore, the amount of adsorbed particles at the oil-water interface is limited which affects the properties of the capsule membranes.

There is therefore a need for an improved system which would be flexible in terms of particle size adjustment, and which would allow a better control on the amount of adsorbed particles in order to improve properties such as the permeability of the system and/or its mechanical properties.

SUMMARY OF THE INVENTION

In a first aspect, the present invention relates to a process for the preparation of an organic-inorganic microcapsule comprising the steps of:
1) suspending in water a first type of inorganic particles with at least one amine functionality and a second type of inorganic particles with at least one hydroxyl functionality, to form an aqueous phase;
2) suspending at least one polyisocyanate in a perfume or flavor oil to form an oil phase;
3) adding the oil phase to the water phase and mixing them to form an oil-in-water Pickering emulsion under conditions allowing interfacial reaction between the at least one polyisocyanate and the functional groups on inorganic particles to form an inorganic-organic microcapsule.

In a second aspect, the invention concerns a microcapsule obtainable by such a process as well as perfuming compositions and perfumed articles containing them.

In a last aspect, the invention relates to the use of inorganic particles of two types in terms of functionalities, for the stabilization of a Pickering emulsion further subjected to an interfacial polymerisation reaction.

DETAILED DESCRIPTION OF THE INVENTION

Unless stated otherwise, percentages (%) are meant to designate percent by weight of a composition.

By "inorganic particles with at least one amine functionality", it is meant that each particle has been functionalised so as to comprise at least one amine moiety such as NH$_2$.

By "inorganic particles with at least one hydroxyl functionality", it is meant that each particle has been functionalised so as to comprise at least one hydroxyl moiety such as OH.

By "perfume or flavour oil", it is meant a single perfuming or flavouring compound or a mixture of several perfuming or flavouring compounds.

By "particle size" it is meant an average diameter of particles based on size distribution measured by dynamic light scattering (DLS) using Zetasizer Nano ZS equipment from Malvern Instruments Ltd., UK when particles are dispersed into a water phase.

By "microcapsules size" it is meant the volume mean diameter (D[4,3]) of the relevant capsules, capsules suspension as obtained by laser light scattering of a diluted sample in a Malvern Mastersizer 3000.

The present invention relates to a process for the preparation of a volatile system for encapsulating an active agent e.g. a perfume oil, with a robust polymeric shell. Said system is flexible in a way that it allows adjusting the properties of the capsules, in particular their size, morphology, permeability, density and surface properties. In particular, a first object of the present invention consists of a process for the preparation of an organic-inorganic microcapsule comprising the steps of:

1) suspending in water a first type of inorganic particles with at least one amine functionality and a second type of inorganic particles with at least one hydroxyl functionality, to form an aqueous phase;
2) suspending at least one polyisocyanate in a perfume or flavor oil to form an oil phase;
3) adding the oil phase to the water phase and mixing them to form an oil-in-water Pickering emulsion under conditions allowing interfacial reaction between the at least one polyisocyanate and the functional groups on inorganic particles to form an inorganic-organic microcapsule in a slurry;
4) optionally drying the obtained microcapsule slurry.

Figure 1:
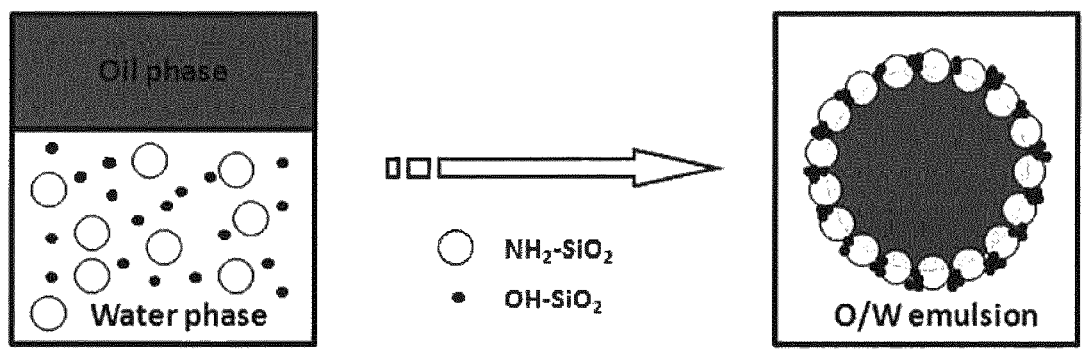
FIG. 1: is a schematic representation of the formation of a Pickering emulsion when a mixture of hydroxyl-$SiO_2$ particles (referred to as OH—$SiO_2$) and amino-$SiO_2$ particles (referred to as $NH_2$—$SiO_2$) is used to stabilize the oil phase.

The process of the invention consists in forming a Pickering emulsion that is further subjected to interfacial reaction that takes place between the polyisocyanate in the oil phase and functional groups on inorganic particles surface which adsorb at the oil/water interface so as to lock the inorganic particles at the oil/water interface and form the hybrid shell. Without wishing to be bound by theory, it is believed that the Pickering emulsion determines the morphology and surface properties (size, density, zeta potential, stiffness) of the membrane, while the interfacial reaction determines the permeability of the hybrid capsules. FIG. 1 schematises the formation of a Pickering emulsion when a mixture of a first type of particles and a second type of particles is used. According to a particular embodiment, the hybrid microcapsules according to the invention are prepared in the absence of any molecular surfactant.

In the first step of the process, the mixed inorganic particles (first type and second type) are dispersed in an aqueous phase with a pH preferably comprised between 2 and 8. Typically this is done using ultrasonic agitation. In a second step, at least one polyisocyanate is dissolved in a perfume or flavour oil to form an oil phase, which is then added to the water phase to form a Pickering emulsion. The oil-in-water Pickering emulsion is made for instance by using high speed mechanical disperser or ultrasonic dispersers at room temperature. Once the Pickering emulsion is formed, the pH value is preferably adjusted to a value above 8.5 and preferably not higher than 11. The interfacial reaction can be carried out typically at a temperature between 50° C. and 80° C. under stirring for 2 to 40 hours to complete the reaction and form inorganic-organic microcapsules in the form of a slurry.

According to a particular embodiment, the oil phase concentration is comprised between 5% and 60%, preferably between 20% and 40% of the Pickering emulsion.

According to a particular embodiment, the process of the invention comprises adding a polyamine or a polyol into the water phase during the reaction process. This additional step allows forming a more compact organic-inorganic shell. Examples of suitable polyamine include guanidine, guanidine salts, guanazole, ethylene diamine, 1,3-diaminopropane, hexamethylenediamine, putrescine, cadaverine, spermidine, spermine, polyallylamine, polyethyleneimine, polyetheramines and polyvinylamine. Examples of suitable polyol include ethylene glycol, glycerol, sucrose, pentaerythritol, polypropylene glycol, polytetrahydrofuran, diethylene glycol and polyethylene glycol.

According to particular embodiment, the surface of the hybrid microcapsules obtained by the process of the invention can be modified with an additional step. Monomers or polymers suitable for surface modification are selected from compounds which can form chemical bond between the monomer or polymer and the microcapsules and which can improve the compatibility between the microcapsules and a target substrate. Typical examples of those compounds include amine, quaternary amines, dopamine, glycidyl ethers, polyols, phenols, aminoacids, saccharides and hydrophilic isocyanates. According to this embodiment, the microcapsules obtained by the process described above are further dispersed in a solution of monomer or polymer mentioned above. This surface modification can be carried out on mild condition optionally in the presence of a catalyst.

According to a particular embodiment, the capsule slurry obtained by any of the above-mentioned processes can further be dried. Any drying method known to a skilled person in the art can be used; in particular the slurry may be spray-dried preferably in the presence of a polymeric carrier material such as polyvinyl acetate, polyvinyl alcohol, dextrines, natural or modified starch, vegetable gums, pectins, xanthanes, alginates, carragenans or cellulose derivatives to provide microcapsules in a powder form.

The capsules obtainable by the above-described process are also an object of the invention.

Figure 2:
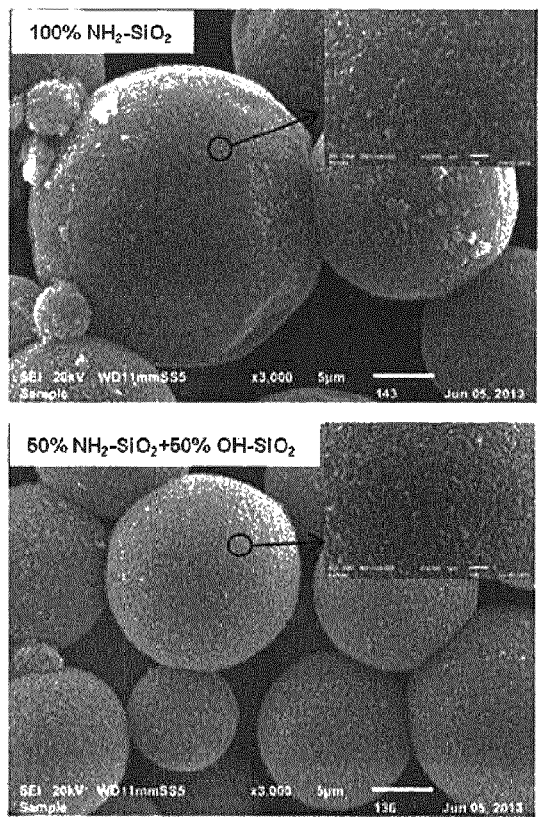
FIG. 2: shows Scanning Electron Microscope (SEM) micrographs illustrating the adsorption of $SiO_2$ at the oil/water interface when using 100% $NH_2$—$SiO_2$, respectively 50% $NH_2$—$SiO_2$+50% OH—$SiO_2$.

The morphology of the microcapsules of the invention can vary from a core-shell to a matrix type. According to one embodiment, it is of the core-shell type. In this case, the microcapsules comprise a core of hydrophobic perfume or flavour oil and a shell comprising a first type of inorganic particles with at least one amine functionality and a second type of inorganic particles with at least one hydroxyl functionality, said particles being selectively cross-linked with a polyisocyanate. The microcapsules are defined as "organic-inorganic" or "hybrid" with reference to the nature of the shell that is composed of at least two types of inorganic particles used to stabilize a Pickering emulsion further subjected to interfacial polymerisation with at least one polyisocyanate. The first type of those particles consists of inorganic particles with at least one amine functionality, here-in referred to as "Type 1" and the second type consists of inorganic particles with at least one hydroxyl functionality, here-in referred to as "Type 2". It has been surprisingly found that using a mixture of those two types of inorganic particles is tremendously improving the microcapsules obtained through a possible adjustment of their properties compared to microcapsules wherein only one type of particles e.g. with amine functionality, was used. In fact, while the latter show little margin for size adjustment but also limited adsorbed functionalised particles at the oil-water interface, which inherently affects the properties of the capsule membrane, the microcapsules obtainable by a process according to the invention allow a better adsorption of particles at the oil-water interface. FIG. 2 shows in this regard a comparison between a system with only one type of particles and one with a mixture of two types of particles. The pictures demonstrate that using a mixture allows to provide a more compact membrane. The improved loading of particles in the capsules and on the membrane increases the density of the capsules compared to the prior art which has also a benefit in terms of suspension of the capsule slurry in a liquid formulation. Moreover, the size of the capsules according to the invention is adjustable as well as the particle content in the membrane of the delivery system. Furthermore, the hybrid microcapsules of the invention proved to allow a tuning of their surface properties as a function of the ratio between the two types of inorganic particles which gives further opportunities for surface modification by using different polymers to further improve the performance of those hybrid systems, in applications such as perfumed consumer product. It has also been observed that in terms of deposition on surfaces, the capsules of the invention perform very well and better than prior art capsules such as polyurea-based capsules functionalized with cationic polymers.

Suitable inorganic particles for the process of the present invention include silica, silicates, titanium dioxide, aluminium oxide, zinc oxide, iron oxide, mica, clays, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, calcium phosphate and diatomaceous earth. Preferably, inorganic particles selected from the group consisting of cosmetic-grade oxides such as silicon dioxide, titanium dioxide and zinc oxide are used. More preferably silica is used.

According to one embodiment, the first type of inorganic particles and the second type or inorganic particles consist of the same material. For instance, in the case of silica, the mixture consists in combining OH—$SiO_2$ with $NH_2$—$SiO_2$. According to another embodiment, the first type of inorganic particles and the second type of inorganic particles consist of different inorganic materials. Preferably, the mixture consists of silicon dioxide with a second type of particles selected from the group consisting of calcium carbonate, calcium phosphate, titanium dioxide and clay.

The size of the particles is typically comprised between 10 and 6000 nm, preferably between 100 and 1000 nm, more preferably between 100 and 500 nm.

According to a preferred embodiment, inorganic particles of Type 1 and Type 2 have different particle sizes. By different particle size it is meant that particle sizes differ by more than 20%. According to another embodiment, inorganic particles of Type 1 and Type 2 have similar sizes i.e. sizes of the same order or magnitude. What is considered as same order of magnitude in the framework of the invention is different by less than 20%.

Figure 3:
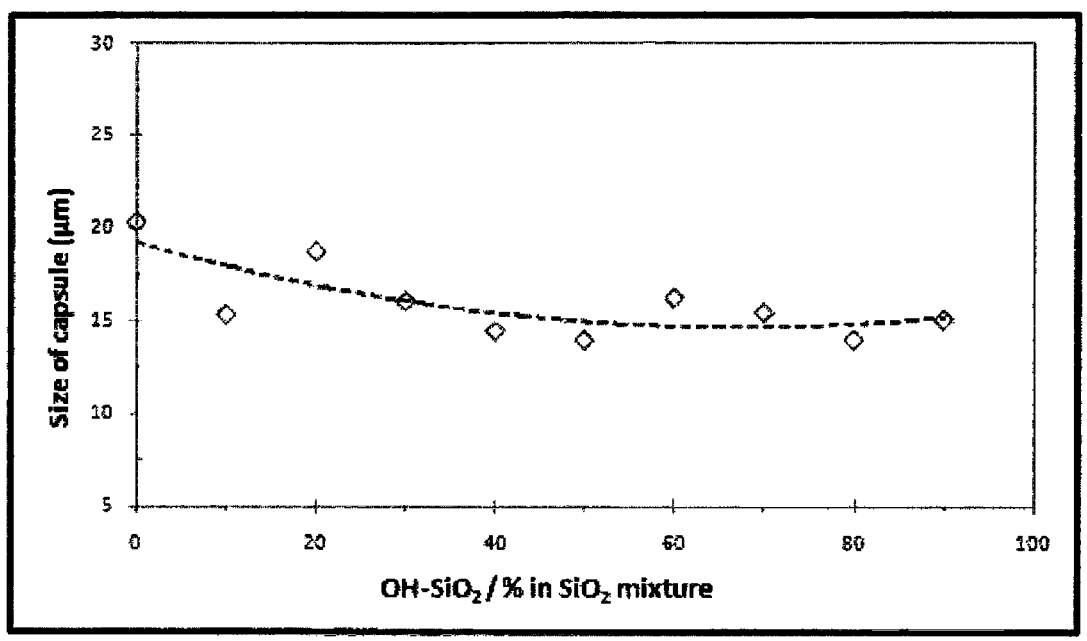
FIG. 3: represents the size of a microcapsule as a function of the percentage of OH—$SiO_2$ in a particle mixture.
Figure 4:
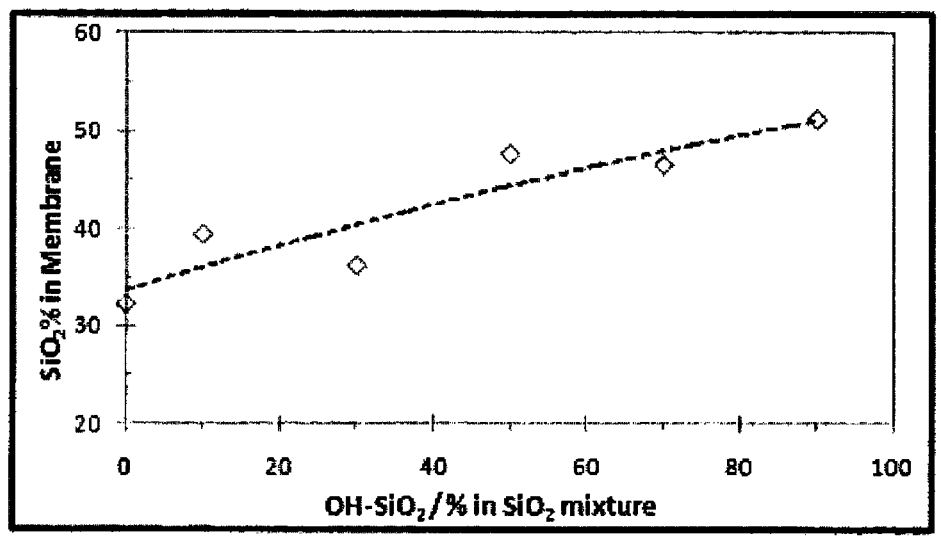
FIG. 4: represents the percentage of $SiO_2$ in the membrane of a capsule as a function of the percentage of OH—$SiO_2$ in the particle mixture.

The ratio used in the preparation of the microcapsules of the invention between Type 1 and Type 2 of inorganic particles is playing a role in the properties of the obtained product. More particularly, by changing said ratio, the adsorption of inorganic particles at the oil/water interface can be controlled. According to the invention, the ratio between Type 1 and Type 2 of inorganic particles is preferably comprised between 0.95 and 0.05, more preferably between 0.7 and 0.3. FIGS. 3 and 4 illustrate the impact of the presence of a second type of particles in different proportions, on the size of the capsule (FIG. 3) and on the percentage of inorganic particles in the membrane of the capsule (FIG. 4). This demonstrates the ability of the system to be adjusted and optimized as a function of the needs.

Preferably, the total amount of inorganic particles present in the aqueous phase is comprised between 0.1 and 20 wt %, more preferably between 0.5 and 5.0 wt %.

Suitable polyisocyanates used according to the invention include aromatic polyisocyanate, aliphatic polyisocyanate and mixtures thereof.

According to one embodiment, said polyisocyanate is an aromatic polyisocyanate. The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

Preferably, the at least one polyisocyanate is hydrophobic.

Preferably, the at least one polyisocyanate is present in an amount comprised between 0.1 wt % and 20 wt % of the oil phase.

The hybrid microcapsules of the invention may encapsulate a perfume or flavour oil. Preferably, the perfume or flavour oil is present in amount ranging from 5% to 60% by weight of the microcapsules suspension. Referring to microcapsule suspension or microcapsule slurry in the context of the invention is equivalent and refers to microcapsules suspension in water. Advantageously, oils that can be successfully encapsulated through the process of the invention have a wide range of hydrophobicities and volatilities. It is also worth mentioning that by "perfuming oil" it is meant here a compound or a mixture of compounds, which is used in a perfuming preparation or a composition to impart a hedonic effect. In other words such compounds, to be considered as being perfuming ones, must be recognized by a person skilled in the art as being able to impart or modify in a positive or pleasant way the odour of a composition, and not just as having an odour. The perfume oil can be a perfuming ingredient alone or a mixture of ingredients in the form of a perfuming composition. Any perfuming ingredient or composition can be used. Typically, perfume oil comprising at least one ingredient with a log P above 1 can be used in the present invention. On the other hand, flavouring oils, i.e. one or several ingredients capable of imparting or modifying the taste of a composition or products are also suitable oils to be encapsulated through the process of the invention. Specific examples of such perfuming or flavouring ingredients may be found in the literature of reference, for example in Perfume and Flavour Chemicals, 1969 (and later editions), by S. Arctander, Montclair N.J. (USA), as well as in the numerous patent and other literature related to the perfume and flavour industry. They are well known to the skilled person in the art of perfuming or flavouring consumer products, that is, or imparting a pleasant odour or a taste to a consumer product.

In the case of perfuming ingredients, they may be dissolved in a solvent of current use in the perfume industry. Examples of such solvents are diethyl phthalate, isopropyl myristate, Abalyn®, benzyl benzoate, ethyl citrate, limonene or other terpenes, or isoparaffins.

Another object of the present invention is a perfuming composition comprising:

(i) Perfume microcapsules as defined above;
(ii) At least one ingredient selected from the group consisting of a perfumery carrier, a perfumery co-ingredient and mixtures thereof;
(iii) Optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in all the fields of modern perfumery, i.e. fine or functional perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

In particular, examples of such formulations can be found in the patents and patent applications relative to such products, for example in WO2008/016684, US2007/0202063, WO2007/062833, WO2007/062733, WO2005/054422, EP1741775, GB2432843, GB2432850, GB2432851, GB2432852, WO 9850011, WO2013174615 or WO2012084904.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such as liquid detergents, all-purpose cleaners, fabric softeners and refreshers, ironing waters and detergents and softener. As detergents we include here products such as detergent compositions or cleaning products for washing up or for cleaning various surfaces, for example intended for the treatment of textiles or hard surfaces (floors, tiles, stone-floors etc.).

Preferably, the consumer product comprises from 0.1 to 15 wt %, more preferably between 0.5 and 5 wt % of the microcapsules of the present invention, these percentages being defined by weight relative to the total weight of the consumer product. Of course the above concentrations may be adapted according to the olfactive effect desired in each product.

The capsules of the invention have proven to be particularly and advantageously stable in consumer products containing significant amount of surfactant and more particularly they demonstrated an improved stability compared to capsules wherein only one type of particles is used.

The invention will now be further described by way of examples. It will be appreciated that the invention as claimed is not intended to be limited in any way by these examples.

EXAMPLES

Example 1

Preparation of Hybrid Microcapsules with Mixture of $SiO_2$ Particles

In the first step, amino-$SiO_2$ particles and hydroxyl-$SiO_2$ particles are dispersed in pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. When stable Pickering emulsion is formed, the pH is adjusted to 9.5 by 5% NaOH aqueous solution. The formulation is described in Table 1 below.

TABLE 1

Formulation of hybrid microcapsules preparation

| Ingredient | Mass/g |
|---|---|
| Amino-$SiO_2$ particles[1] | 0.2625 |
| Hydroxyl-$SiO_2$ particles[2] | 0.2625 |
| pH 7 buffer[3] | 34.475 |
| Desmodur ® N 100[4] | 0.625 |
| Takenate ® D-110 N[5] | 0.24 |
| Perfume oil[6] | 14.135 |

[1]Silicon Oxide particles modified with amino group, origin: SkySpring Nanomaterials, Inc.
[2]Pyrogenic Silica HDK ® N20, origin: Wacker Chemie AG.
[3]Di-Sodium hydrogen phosphate and Potassium dihydrogen phosphate buffer solution (pH 7.0)
[4]Biuret of hexamethylene diisocyanate, origin: Bayer
[5]Trimethylol propane-adduct of xylylene diisocyanate, origin: Mitsui
[6]Mixture of an equal mass of Salicynile [(2Z)-2-PHENYL-2-HEXENENITRILE], Cyclosal [(+−)-3-(4-ISOPROPYLPHENYL)-2-METHYLPROPANAL], Ramascone [(+−)-METHYL 2,2-DIMETHYL-6-METHYLENE-1-CYCLOHEXANECARBOXYLATE], Verdox ™ (tradename from IFF) [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stirring. After 10 min, 3 ml 5.2% Guanidine Carbonate (form Acros Organics) solution is added into the reaction system drop wisely in 10 min. Then the reaction is carried out at 70° C. for another 3 h under stirring. The pH value is maintained above 8.5 during the reaction.

The obtained microcapsules are in the form of a slurry (suspension in water).

Example 2

Comparative Example Between Capsules According to the Invention and Capsules Prepared with One Type of Particles (Amino-$SiO_2$ Particles)

Measurement Method For Particle Loading on Capsule or in Membrane (Same For All Examples):

Experiments are carried out on a Thermogravimetric Analyzer (TGA/DSC 1, Mettler-Toledo) equipped with a microbalance having an accuracy of 1 µg.

The microcapsule slurry is centrifugated 3 times to remove the free dispersed $SiO_2$ particles in water phase, and then microcapsule sample is introduced into an aluminium oxide crucible and the mass change is monitored under controlled temperature with a constant flow of nitrogen of 20 ml/min. The measurement starts at 25° C. and the temperature is increased to 80° C. at a rate of 10° C./min (keep at 80° C. for 120 minutes), then the temperature is increased to 700° C. at a rate of 10° C./min (keep at 700° C. for 120 minutes). The particle loading on capsule or in membrane is calculated according to the TGA curve.

Preparation of Benchmark Hybrid Capsules with Amino-$SiO_2$ Particles

In the first step, amino-$SiO_2$ particles are dispersed in pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. When stable Pickering emulsion is formed, the pH is adjusted to 9.5 by 5% NaOHaq solution. The formulation is described in Table below.

TABLE 2

Formulation of hybrid microcapsules preparation

| Ingredient | Mass/g |
| --- | --- |
| Amino-SiO$_2$ particles[1] | 0.525 |
| pH 7 buffer[2] | 34.475 |
| Desmodur ® N 100[3] | 0.625 |
| Takenate ® D-110 N[4] | 0.24 |
| Perfume oil[5] | 14.135 |

[1] Silicon Oxide particles modified with amino group, origin: SkySpring Nanomaterials, Inc.
[2] Di-Sodium hydrogen phosphate and Potassium dihydrogen phosphate buffer solution (pH 7.0)
[3] Biuret of hexamethylene diisocynate, origin: Bayer
[4] Trimethylol propane-adduct of xylylene diisocyanate, origin: Mitsui Chemicals
[5] Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXYLATE], Verdox ™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stiffing. After 10 min, 3 ml 5.2% Guanidine Carbonate (form Acros Organics) solution is added into the reaction system dropwisely in 10 min. Then the reaction is carried out at 70° C. for another 3 h under stirring. The pH value is maintained above 8.5 during the reaction. The obtained microcapsules are in the form of a slurry.

Benchmark capsules are characterised as follows:
Ave. Size: D[4,3]=19.4 μm (measured by Mastersizer 3000, from Malvern Instruments Ltd., UK)
Zeta Potential=34.7±1.4 my (measured by Nano ZS, Malvern UK)
Particles loading on capsule: 0.9%/in membrane: 32.25%

Capsules prepared according to Example 1 are characterised as follows:
Ave. Size: D[4,3]=14.9 μm (measured by Mastersizer 3000, from Malvern Instruments Ltd., UK)
Zeta Potential=−4.3±0.4 my (measured by nano zs, Malvern UK)
Particle loading on capsule: 2.3%/in membrane: 47.73%

The hybrid capsules prepared with mixture of amino-SiO$_2$ particles and hydroxyl-SiO$_2$ particles show higher particle loading (on the capsules and in the membranes) compared with the benchmark capsules (hybrid capsules prepared with amino-SiO$_2$ particles). Higher particle loading gives better mechanical properties to the hybrid capsules.

Example 3

Preparation of Hybrid Capsules with a Mixture of Amino-SiO$_2$ Particles and Hydroxyapatite Particles (Benchmark Capsules as Described in Example 2)

In the first step, amino-SiO$_2$ particles and hydroxyapatite particles are dispersed into pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. The formulation is described in Table below.

TABLE 3

Formulation of hybrid microcapsules preparation

| Ingredient | Mass/g |
| --- | --- |
| Amino-SiO$_2$ particles[1] | 0.42 |
| Hydroxyapatitle particles[2] | 0.105 |
| pH 7 buffer[3] | 34.475 |
| Desmodur ® N 100[4] | 0.625 |
| Takenate ® D-110 N[5] | 0.24 |
| Perfume oil[6] | 14.135 |

[1] Silicon Oxide particles modified with amino group, origin: SkySpring Nanomaterials, Inc.
[2] Hydroxyapatite particles, origin: Aladdin Chemistry Co. Ltd
[3] Di-Sodium hydrogen phosphate and Potassium dihydrogen phosphate buffer solution (pH 7.00)
[4] Biuret of hexamethylene diisocynate, origin: Bayer
[5] Trimethylol propane-adduct of xylylene diisocyanate, origin: Mitsui Chemicals
[6] Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXYLATE], Verdox ™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stirring. After 10 min, 3 ml 5.2% Guanidine Carbonate (form Acros Organics) solution is added into the reaction system dropwisely in 10 min. Then the reaction is carried out at 70° C. for another 3 h under stirring. The obtained microcapsules are in the form of a slurry (suspension in water).

Ave. Size: D[4,3]=19.4 μm (measured by Mastersizer 3000, from Malvern Instruments Ltd., UK)
Zeta Potential=−2.7±2.3 my (measured by nano zs, Malvern UK)
Particles loading on capsule: 3.2%/in membrane: 44.23%

The hybrid capsules prepared with mixture of amino-SiO$_2$ particles and hydroxyapatite particles show higher particle loading (on the capsules, 3.2% vs 0.9% and in the membrane) compared with the benchmark capsules (hybrid capsules prepared with amino-SiO$_2$ particles).

Example 4

Preparation of Hybrid Capsules with Mixture of Amino-SiO2 Particles and TiO$_2$ Particles (Benchmark Capsules from Example 2)

In the first step, amino-SiO$_2$ particles and TiO$_2$ particles are dispersed into pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. The formulation is described in Table below.

TABLE 4

Formulation of hybrid microcapsules preparation

| Ingredient | Mass/g |
| --- | --- |
| Amino-SiO$_2$ particles[1] | 0.42 |
| TiO$_2$ particles[2] | 0.105 |
| pH 7 buffer[3] | 34.475 |
| Desmodur ® N 100[4] | 0.625 |
| Takenate ® D-110 N[5] | 0.24 |
| Perfume oil[6] | 14.135 |

[1] Silicon Oxide particles modified with amino group, origin: SkySpring Nanomaterials, Inc.
[2] Titanium dioxide particles (Rutile, hydrophilic), origin: Aladdin Chemistry Co. Ltd
[3] Di-Sodium hydrogen phosphate and Potassium dihydrogen phosphate buffer solution (pH 7.00)
[4] Biuret of hexamethylene diisocynate, origin: Bayer
[5] Trimethylol propane-adduct of xylylene diisocyanate, origin: Mitsui Chemicals
[6] Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXYLATE], Verdox ™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stirring. After 10 min, 3 ml 5.2% Guanidine Carbonate (form Acros Organics) solution is added into the reaction system dropwisely in 10 min. Then the reaction is carried out at 70° C. for another 3 h under stirring. The obtained microcapsules are in the form of a slurry (suspension in water).

Ave. Size: D[4,3]=21.4 µm (measured by Mastersizer 3000, from Malvern Instruments Ltd., UK)

Zeta Potential=15.6±4.8 my (measured by nano zs, Malvern UK)

Particles loading on capsule: 3.4%/in membrane: 46.90%

The hybrid capsules prepared with mixture of amino-$SiO_2$ particles and $TiO_2$ particles show higher particle loading (on the capsules, 3.4% vs 0.9% and in membrane) compared with the benchmark capsules (hybrid capsules prepared with amino-$SiO_2$ particles).

Example 5

Preparation of Hybrid Capsules with Mixture of Amino-$SiO_2$ Particles and $CaCO_3$ Particles (Benchmark Capsules—Example 2)

In the first step, amino-$SiO_2$ particles and $CaCO_3$ particles are dispersed into pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. The formulation is described in Table below.

TABLE 5

Formulation of hybrid microcapsules preparation

| Ingredient | Mass/g |
|---|---|
| Amino-$SiO_2$ particles[1] | 0.2625 |
| $CaCO_3$ particles[2] | 0.2625 |
| pH 7 buffer[3] | 34.475 |
| Desmodur ® N 100[4] | 0.625 |
| Takenate ® D-110 N[5] | 0.24 |
| Perfume oil[6] | 14.135 |

[1]Silicon Oxide particles modified with amino group, origin: SkySpring Nanomaterials, Inc.
[2]Calcium carbonate, origin: BoYu GaoKe Co. Ltd
[3]Di-Sodium hydrogen phosphate and Potassium dihydrogen phosphate buffer solution (pH 7.00)
[4]Biuret of hexamethylene diisocynate, origin: Bayer
[5]Trimethylol propane-adduct of xylylene diisocyanate, origin: Mitsui Chemicals
[6]Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXYLATE], Verdox ™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stiffing. After 10 min, 3 ml 5.2% Guanidine Carbonate (form Acros Organics) solution is added into the reaction system dropwisely in 10 min. Then the reaction is carried out at 70° C. for another 3 h under stirring. The obtained microcapsules are in the form of a slurry (suspension in water).

Ave. Size: D[4,3]=22 µm (measured by Mastersizer 3000, from Malvern Instruments Ltd., UK)

Zeta Potential=4.6±0.8 my (measured by Nano ZS, Malvern UK)

$SiO_2$ loading on capsule: 3.4%/in membrane: 50%

The hybrid capsules prepared with mixture of amino-$SiO_2$ particles and $CaCO_3$ particles show higher particle loading (on the capsules, 3.4% vs 0.9% and in membrane) compared with the benchmark capsules (hybrid capsules prepared with amino-$SiO_2$ particles).

Example 6

Preparation of Hybrid Capsules with Mixture of Amino-$SiO_2$ Particles and Clay Particles (Benchmark Capsules from Example 2)

In the first step, amino-$SiO_2$ particles and clay particles are dispersed into pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. The formulation is described in Table below.

TABLE 6

Formulation of hybrid microcapsules preparation

| Ingredient | Mass/g |
|---|---|
| Amino-$SiO_2$ particles[1] | 0.3675 |
| Laponite XLG particles[2] | 0.1575 |
| pH 7 buffer[3] | 34.475 |
| Desmodur ® N 100[4] | 0.625 |
| Takenate ® D-110 N[5] | 0.24 |
| Perfume oil[6] | 14.135 |

[1]Silicon Oxide particles modified with amino group, origin: SkySpring Nanomaterials, Inc.
[2]Laponite XLG particles, origin: Rockwood
[3]Di-Sodium hydrogen phosphate and Potassium dihydrogen phosphate buffer solution (pH 7.00)
[4]Biuret of hexamethylene diisocynate, origin: Bayer
[5]Trimethylol propane-adduct of xylylene diisocyanate, origin: Mitsui Chemicals
[6]Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXYLATE], Verdox ™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stirring. After 10 min, 3 ml 5.2% Guanidine Carbonate (form Acros Organics) solution is added into the reaction system dropwisely in 10 min. Then the reaction is carried out at 70° C. for another 3 h under stirring. The obtained microcapsules are in the form of a slurry (suspension in water).

Ave. Size: D[4,3]=19.8 µm (measured by Mastersizer 3000, from Malvern Instruments Ltd., UK)

Zeta Potential=−1.26±1.6 my (measured as in other examples)

Particles loading on capsule: 3.5%/in membrane: 44.4%

The hybrid capsules prepared with mixture of amino-$SiO_2$ particles and Clay particles show higher particle loading (on the capsules, 3.5% vs 0.9% and in membrane) compared with the benchmark capsules (hybrid capsules prepared with amino-$SiO_2$ particles).

Example 7

Preparation of Hybrid Capsules with Mixture of Amino-$SiO_2$ Particles and Kaolin Particles (Benchmark Capsules—Example 2)

In the first step, amino-$SiO_2$ particles and Kaolin particles (superfine) are dispersed into pH 7 buffer solution using ultrasonic probe. Then the oil phase with crosslinking agent is mixed with aqueous phase. Pickering emulsion is made by using an homogenizer, Ultra Turrax, IKA T25, at 24 000 rpm for 5 min. The formulation is described in Table below.

TABLE 7

Formulation of hybrid microcapsules preparation

| Ingredient | Mass/g |
| --- | --- |
| Amino-SiO$_2$ particles[1] | 0.315 |
| Kaolin particles[2] | 0.21 |
| pH 7 buffer[3] | 34.475 |
| Desmodur ® N 100[4] | 0.625 |
| Takenate ® D-110 N[5] | 0.24 |
| Perfume oil[6] | 14.135 |

[1]Silicon Oxide Nanoparticles modified with amino group, from SkySpring Nanomaterials, Inc.
[2]Kaolin particles (superfine), from Aladdin Chemistry Co. Ltd
[3]Di-Sodium hydrogen phosphate and Potassium dihydrogen phosphate buffer solution (pH 7.00)
[4]Biuret of hexamethylene diisocynate, origin: Bayer
[5]Trimethylol propane-adduct of xylylene diisocyanate, origin: Mitsui Chemicals
[6]Mixture of an equal mass of Salicynile [(2Z)-2-PHENYL-2-HEXENENITRILE], Cyclosal [(+−)-3-(4-ISOPROPYLPHENYL)-2-METHYLPROPANAL], Romascone [(+−)-METHYL 2,2-DIMETHYL-6-METHYLENE-1-CYCLOHEXANECARBOXY-LATE], Verdox™ [mixture of (+−)-CIS-2-TERT-BUTYL-1-CYCLOHEXYL ACETATE and (+−)-TRANS-2-TERT-BUTYL-1-CYCLOHEXYL ACETATE] and Dorisyl [mixture of TRANS-4-TERT-BUTYL-1-CYCLOHEXYL ACETATE and CIS-4-TERT-BUTYL-1-CYCLOHEXYL ACETATE]

In the second step, interfacial reaction is carried out at 70° C. under stirring. After 10 min, 3 ml 5.2% Guanidine Carbonate (form Acros Organics) solution is added into the reaction system dropwisely in 10 min. Then the reaction is carried out at 70° C. for another 3 h under stirring. The obtained microcapsules are in the form of a slurry (suspension in water).

Ave. Size: D[4,3]=24.3 μm (measured by Mastersizer 3000, from Malvern Instruments Ltd., UK)

Zeta Potential=2.3±0.2 my (measured as in other examples)

SiO$_2$ loading on capsule: 3.3%/in membrane: 43.24%

The hybrid capsules prepared with mixture of amino-SiO$_2$ particles and Kaolin particles show higher particle loading (on the capsules, 3.3% vs 0.9% and in membrane) compared with the benchmark capsules (hybrid capsules prepared with amino-SiO$_2$ particles).

Example 8

Surface Modification of Hybrid Microcapsules

The free dispersed SiO$_2$ particles in hybrid microcapsules slurry as described in example 1 are removed by using centrifugation. The hybrid microcapsules are re-dispersed in 2 mg/ml Dopamine solution (Dopamine is dissolved in 10 mM Tris-HCl pH 8.5 buffer solution). The suspension is shaken at room temperature for 8 h. Then, the obtained microcapsules are washed with de-ionized water.

Example 9

Comparative Example of Stability in a Shower Gel

A predetermined amount of hybrid microcapsules slurry as described in example 1 was added into a shower gel base under rapid stirring (1200 RPM for 10 min). The shower gel base contained 8.0% Carbopol® Aqua CC polymer (Polyacrylate-1 crosspolymer, origin: Noveon), 0.5% Citric acid (40% solution in water), 25.0% Zetesol AO 328 U (Sodium C$_{12}$-C$_{15}$ pareth sulfate, origin: Zschimmer & Schwarz), 4.0% Tego Betain F 50 (Cocamidopropyl betaine, origin: Goldschmidt AG), 0.1% Glydant Plus Liquid (DMDM hydantoin and iodopropynyl butylcarbamate, origin: Lonza), 4.0% Sodium Chloride (20% solution in water) and 58.4% Water. The final encapsulated perfume oil content in the base was equal to 0.2%. The shower gel base containing microcapsules was transferred into closed small bottles and kept at 43° C.

After 2 months storage at 43° C., 2.0 g the shower gel base was mixed with 4.0 ml of deionized water and extracted by 10.0 ml Internal Standard Solution (75 mg/L Ethyl Laurate in Isooctane) with TURBULA® System Schatz-Mixer. Then the organic phase was analyzed by GC (6890N, Agilent Technologies)-MS (5975, Agilent Technologies) to measure the leakage of encapsulated perfume.

Figure 5:
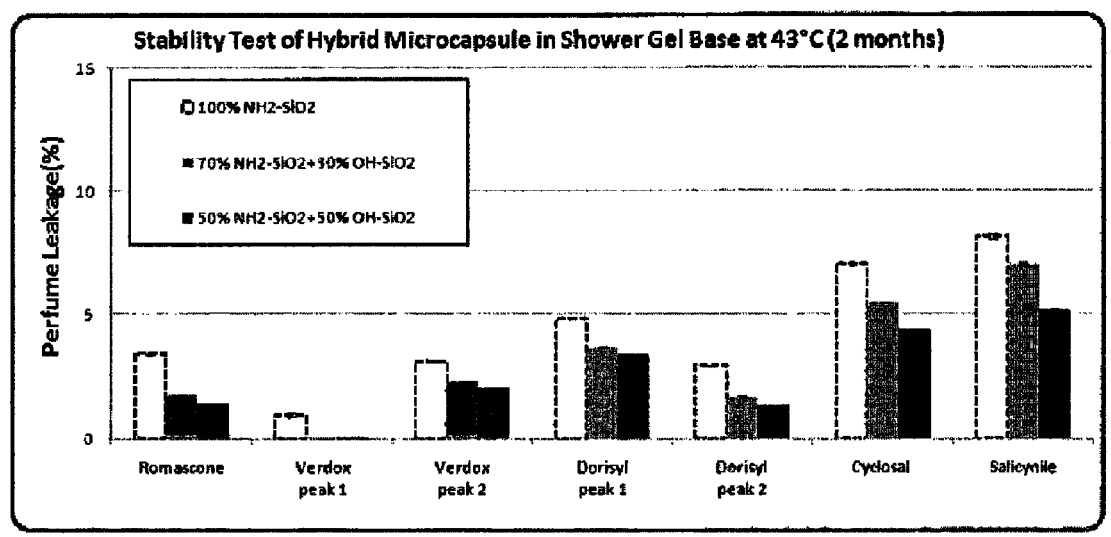
FIG. 5: represents stability results in a shower gel application when comparing a system with one type of particles, versus a system with a mixture of two types of particles.

Stability was tested with microcapsules prepared as described in example 1, comparing different ratios between Type 1 and Type 2 particles and also a system based on 100% type 1 of particles (prior art). The results are shown on FIG. 5. Peak 1 of Verdox™ is from the CIS-Verdox, while peak 2 is from TRANS-Verdox, Peak 2 of Dorisyl is from CIS-Dorisyl and peak 2 is from TRANS-Dorisyl.

With SiO$_2$ mixture, as increasing OH—SiO$_2$, the hybrid microcapsules indicate better storage stability. This result totally matches SEM micrographs in FIG. 2, where more compact membrane corresponds to better storage stability.

Example 10

Panel Test

A predetermined amount of hybrid microcapsules slurry from example 1 was dispersed into the shower gel base as described in example 3. The final encapsulated perfume oil content in the base was equal to 0.25%. During the test, hybrid microcapsules with 100% NH$_2$—SiO$_2$ were used as the reference/benchmark.

7 to 9 expert panelists were selected for each evaluation. Samples of same quantity of shower gel were applied on both forearms following a precise protocol of deposition, washing, rinsing and drying. One of the two samples contained hybrid microcapsules according to the invention while another contained reference microcapsules.

The evaluation of both forearms occurred at the same time and was done in "blind". The panelists evaluated their arms 5 minutes after drying, before rubbing (BR) and after rubbing (AR). And at the given time, 4 hours, 6 hours and 8 hours after drying, the panelists did the same evaluation. Evaluation of Fragrance Intensity on a scale from 0 to 7, 0 meant no odor while 7 meant very strong.

Figure 6:
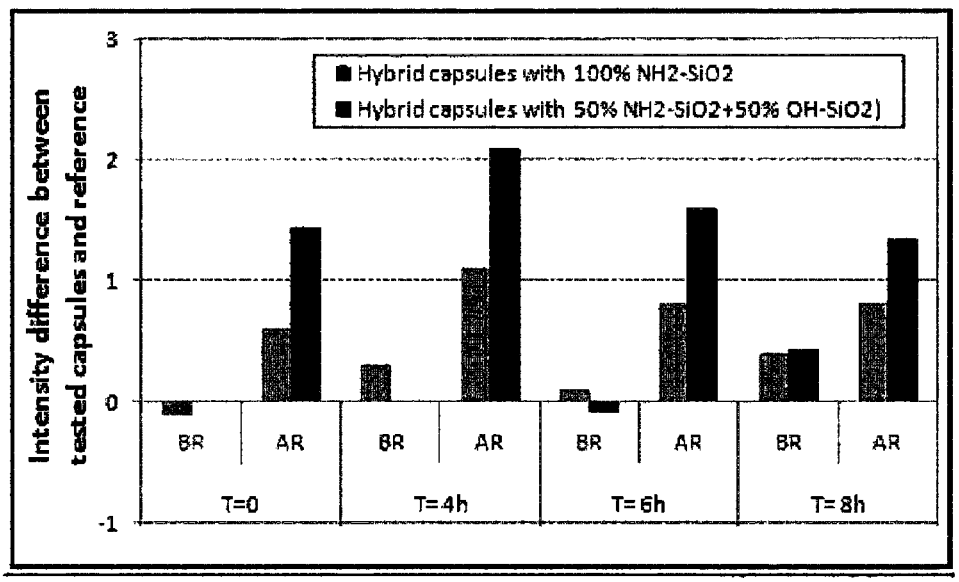
FIG. 6: represents the perceived intensity of a perfume measured in a panel test comparing hybrid microcapsule prepared with 100% NH$_2$—SiO$_2$ versus hybrid microcapsule prepared with 50% NH$_2$—SiO$_2$+50% OH—SiO$_2$.

Results are shown on FIG. 6. It can be concluded that while no significant difference was observed before rubbing, there was a significant improvement with the system according to the invention after rubbing.

What is claimed is:

1. A process for the preparation of an organic-inorganic microcapsule comprising the steps of:
   1) suspending in water first inorganic particles having at least one amine functionality and second inorganic particles having at least one hydroxyl functionality, to form an aqueous phase;
   2) suspending at least one polyisocyanate in a perfume or flavor oil to form an oil phase;
   3) adding the oil phase to the water phase and mixing them to form an oil-in-water Pickering emulsion under conditions allowing interfacial reaction between the at least one polyisocyanate and the functional groups on the first and second inorganic particles to form an inorganic-organic microcapsule, wherein the first and second inorganic particles are selectively cross-linked in the emulsion with the at least one polyisocyanate.

2. A process according to claim 1, wherein the pH of the aqueous phase is adjusted to a value comprised between 2 and 8 and the pH of the formed Pickering emulsion is adjusted to a value comprised between 8.5 and 11.

3. A process according to claim 1, wherein the oil phase represents between 5 and 60% or between 20 and 40% of the Pickering emulsion.

4. A process according to claim 1, which further comprises the step of dispersing the microcapsule in a solution of monomer or polymer selected from the group consisting of amine, quaternary amines, dopamine, glycidyl ether, polyols, phenols, aminoacids, saccharide and hydrophilic isocyante.

5. A process according to claim 1, wherein the inorganic particles are selected from the group consisting of silica, silicates, titanium dioxide, aluminium oxide, zinc oxide, iron oxide, mica, clays, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, calcium phosphate and diatomaceous earth.

6. A process according to claim 1, wherein the first type of inorganic particles and the second type of inorganic particles consist of the same inorganic material.

7. A process according to claim 6, wherein the inorganic nanoparticles consist of silica.

8. A process according to claim 1, wherein the ratio between the first type of inorganic particles and the second type of inorganic particles is comprised between 0.95 and 0.05.

9. A process according to claim 1, wherein the total amount of inorganic nanoparticles present in the aqueous phase is comprised between 0.1 and 20 wt % or between 0.5 and 5.0 wt % of the aqueous phase.

10. A process according to claim 1, wherein the polyisocyanate is present in an amount comprised between 0.1 and 20 wt % of the oil phase.

11. An organic-inorganic microcapsule obtainable by a process as defined in claim 1.

12. An organic-inorganic microcapsule according to claim 11, comprising
 a) a core of hydrophobic perfume or flavor;
 b) a shell comprising a mixture of first inorganic particles having at least one amine functionality and second inorganic particles having at least one hydroxyl functionality, said particles being selectively cross-linked in the mixture with a polyisocyanate.

13. A perfuming composition comprising
 (i) at least one microcapsule according to claim 11;
 (ii) at least one ingredient selected from the group consisting of a perfumery carrier, a perfuming co-ingredient and mixtures thereof;
 (iii) optionally a solvent or adjuvant.

14. A perfumed consumer product comprising as a perfuming ingredient, at least one microcapsule according to claim 11.

15. A perfumed consumer product according to claim 14, in the form of a home care or personal care product selected from the group consisting of a skin cleansing product, a shampoo, a rinse-off conditioner, a deodorant, an antiperspirant, a body lotion, a leave-on conditioner, a fabric conditioner, a liquid detergent, a powder detergent and an all propose cleaner.

16. A process according to claim 2, wherein the oil phase represents between 5 and 60% or between 20 and 40% of the Pickering emulsion.

17. A process according to claim 2, which further comprises the step of dispersing the microcapsule in a solution of monomer or polymer selected from the group consisting of amine, quaternary amines, dopamine, glycidyl ether, polyols, phenols, aminoacids, saccharide and hydrophilic isocyante.

18. A perfuming composition comprising
 (i) at least one microcapsule according to claim 12;
 (ii) at least one ingredient selected from the group consisting of a perfumery carrier, a perfuming co-ingredient and mixtures thereof;
 (iii) optionally a solvent or adjuvant.

19. A perfumed consumer product comprising as a perfuming ingredient, at least one microcapsule according to claim 12.

20. A perfumed consumer product according to claim 19, in the form of a home care or personal care product selected from the group consisting of a skin cleansing product, a shampoo, a rinse-off conditioner, a deodorant, an antiperspirant, a body lotion, a leave-on conditioner, a fabric conditioner, a liquid detergent, a powder detergent and an all propose cleaner.

* * * * *

UNITED STATES PATENT AND TRADEMARK OFFICE
CERTIFICATE OF CORRECTION

PATENT NO. : 9,962,674 B2
APPLICATION NO. : 15/106151
DATED : May 8, 2018
INVENTOR(S) : Wu et al.

It is certified that error appears in the above-identified patent and that said Letters Patent is hereby corrected as shown below:

Column 17:
Lines 37-38, after "12. An organic-inorganic microcapsule", delete "according to claim 11".

Signed and Sealed this
Twenty-sixth Day of June, 2018

Andrei Iancu
*Director of the United States Patent and Trademark Office*